US012653767B2

(12) United States Patent
Pi et al.

(10) Patent No.: US 12,653,767 B2
(45) Date of Patent: Jun. 16, 2026

(54) AQUEOUS SOLUTION FOR SOLUBILIZING SALICYLIC ACID, A METHOD FOR PREPARATION THEREOF, AND A COSMETIC COMPOSITION COMPRISING THE SAME

(71) Applicant: AMOREPACIFIC CORPORATION, Seoul (KR)

(72) Inventors: Bongsoo Pi, Yongin-si (KR); Jin Nam, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 400 days.

(21) Appl. No.: 18/183,795

(22) Filed: Mar. 14, 2023

(65) Prior Publication Data

US 2023/0210737 A1     Jul. 6, 2023

Related U.S. Application Data

(63) Continuation of application No. 16/189,467, filed on Nov. 13, 2018, now abandoned.

(30) Foreign Application Priority Data

Nov. 24, 2017     (KR) ........................ 10-2017-0158787
Jul. 24, 2018     (KR) ........................ 10-2018-0085975

(51) Int. Cl.
| | |
|---|---|
| *A61K 8/368* | (2006.01) |
| *A61K 8/06* | (2006.01) |
| *A61K 8/22* | (2006.01) |
| *A61K 8/41* | (2006.01) |
| *A61K 8/44* | (2006.01) |
| *A61K 8/49* | (2006.01) |
| *A61K 8/67* | (2006.01) |
| *A61K 8/9722* | (2017.01) |
| *A61K 8/9741* | (2017.01) |
| *A61Q 19/00* | (2006.01) |
| *A61Q 19/08* | (2006.01) |

(52) U.S. Cl.
CPC ................ *A61K 8/368* (2013.01); *A61K 8/06* (2013.01); *A61K 8/062* (2013.01); *A61K 8/064* (2013.01); *A61K 8/22* (2013.01); *A61K 8/41* (2013.01); *A61K 8/44* (2013.01); *A61K 8/4953* (2013.01); *A61K 8/673* (2013.01); *A61K 8/9722* (2017.08); *A61K 8/9741* (2017.08); *A61Q 19/00* (2013.01); *A61Q 19/08* (2013.01); *A61K 2800/48* (2013.01); *A61K 2800/52* (2013.01); *A61K 2800/522* (2013.01)

(58) Field of Classification Search
CPC ...... A61K 8/368; A61K 8/974; A61K 8/9722; A61K 8/06; A61K 8/062; A61K 8/064; A61K 8/22; A61K 8/41; A61K 8/44; A61K 8/4953; A61K 8/673; A61K 2800/48; A61K 2800/52; A61K 2800/522; A61Q 19/00; A61Q 19/08
See application file for complete search history.

(56) References Cited

U.S. PATENT DOCUMENTS

| | | |
|---|---|---|
| 5,531,993 A | 7/1996 | Griat |
| 6,143,282 A | 11/2000 | Hansenne et al. |
| 6,248,731 B1 | 6/2001 | Blahut |
| 6,635,702 B1 | 10/2003 | Schmucker-Castner et al. |

FOREIGN PATENT DOCUMENTS

| | | | |
|---|---|---|---|
| CN | 1422147 A | | 6/2003 |
| JP | 2005-200430 A | | 7/2005 |
| KR | 10-1544018 B1 | | 8/2015 |
| RU | 2481845 C2 | * | 5/2013 |
| WO | 2001/076552 A2 | | 10/2001 |

OTHER PUBLICATIONS

Omelyanchuk, P. A., et al. (PE2E translation of RU 2481845 C2, May 20, 2013) (Year: 2013).*
Herman, et al., (2013) Caffeine's mechanism of action and its cosmetic use. Skin Pharmacol Phydiol. 26(1):8-14. Epub 2012 (Year: 2013).*
Mullin, J.W.. (2001). Crystallization (4th Edition)—Appendix. (p. 478). Elsevier (Year: 2001).*
Zhong, J., et al. (Sep. 14, 2017). Measurement and Correlation of Solubility of Theobromine, Theophylline, and Caffeine in Water and Organic Solvents at Various Temperatures. Journal of Chemical & Engineering Data, 62 (9), 2570-2577 (Year: 2017).*
Office Action for CN Patent Application No. 201811431373.9 issued on Jul. 27, 2022. (6 pages).
Zhu Zhaojing et al., "Pharmaceuticals", Fourth Military Medical University Press, 2007, vol. 8, No. 44 ( ** mentioned in the Second Office Action for Chinese Patent Application No. 2018114313739 issued Jan. 18, 2023).
The Second Office Action for Chinese Patent Application No. 2018114313739 (Jan. 18, 2023).

* cited by examiner

*Primary Examiner* — Sue X Liu
*Assistant Examiner* — Susannah S Armstrong
(74) *Attorney, Agent, or Firm* — Merchant & Gould P.C.

(57) ABSTRACT

The present invention provides a salicylic acid aqueous solution comprising salicylic acid, tromethamine as a dissolution-enhancing agent to enhance dissolution of salicylic acid, and water for dissolving salicylic acid.

10 Claims, 1 Drawing Sheet

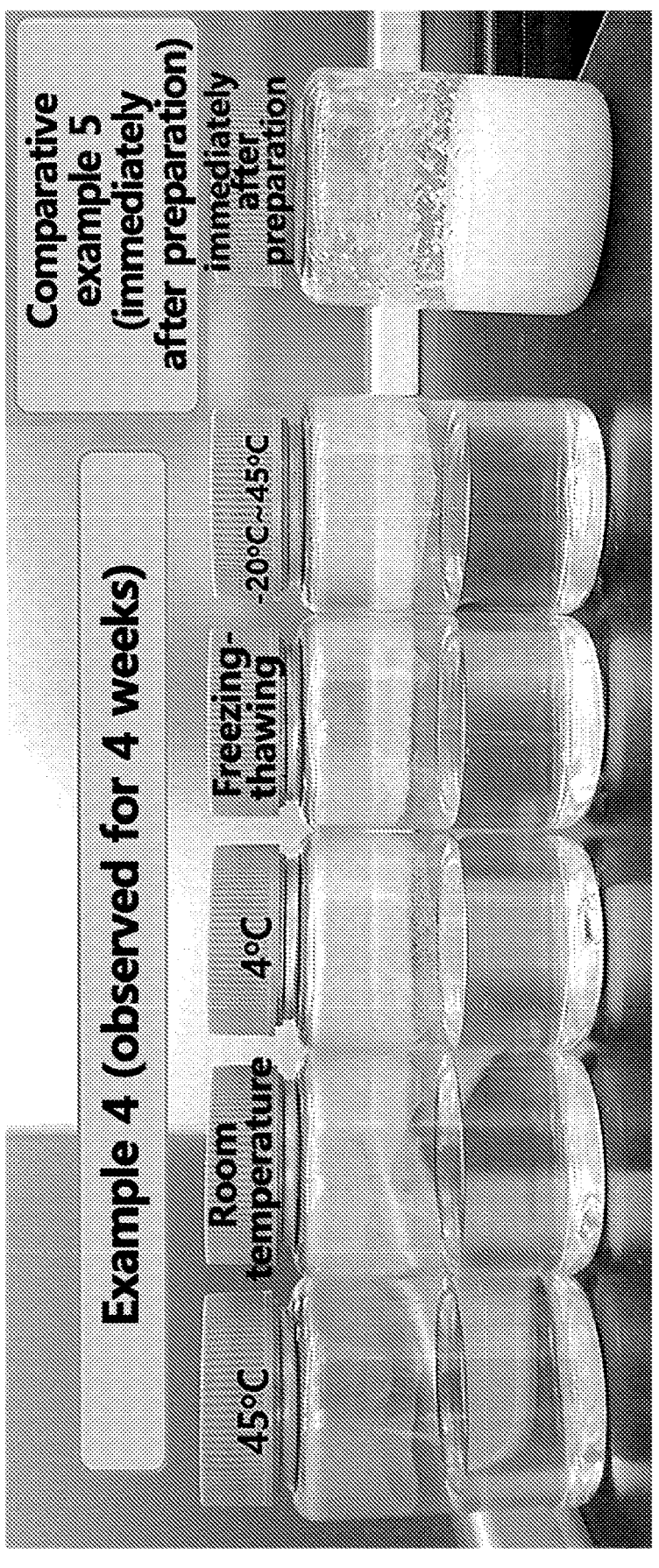

AQUEOUS SOLUTION FOR SOLUBILIZING SALICYLIC ACID, A METHOD FOR PREPARATION THEREOF, AND A COSMETIC COMPOSITION COMPRISING THE SAME

CROSS-REFERENCE TO RELATED APPLICATION

This application is a Continuation of U.S. application Ser. No. 16/189,467, filed on Nov. 13, 2018, which claims the priority of Korean Patent Application No. 10-2017-0158787, filed on Nov. 24, 2017 and No. 10-2018-0085975, filed on Jul. 24, 2018, and all the benefits accruing therefrom under 35 U.S.C. § 119, the contents of which in its entirety are herein incorporated by reference.

BACKGROUND OF THE INVENTION

Field of the Invention

The present invention relates to a salicylic acid aqueous solution having enhanced water-solubility of salicylic acid as an insoluble material, a method for preparation thereof, and a cosmetic composition comprising the same.

Description of the Related Art

Salicylic acid is a representative insoluble material. To use salicylic acid in a cosmetic formulation, especially a solubilizing formulation, an amount of solvent (ethanol) should be increased proportionally to an amount of salicylic acid contained in the formulation. Therefore, to dissolve an amount of salicylic acid in ethanol, ethanol with a weight of at least 10 times should be used. If a high amount of ethanol of more than 10 wt % or 15 wt % is used in a cosmetic formulation, there is a problem that adverse effects such as severe skin irritation is caused.

When salicylic acid is contained in a solubilizing formulation without sufficient solvent, there is a problem that crystals of salicylic acid are precipitated due to a molecular structure of salicylic acid to be favorably crystallized through n bonds between benzene molecules.

SUMMARY OF THE INVENTION

In an aspect, the present invention relates to a cosmetic composition having salicylic acid stabilized without ethanol. Specifically, the present invention relates to a technique for largely enhancing the solubility of salicylic acid through iconic bonds between salicylic acid and dissolution-enhancing agent by dissolving salicylic acid and tromethamine as a dissolution-enhancing agent in water at an elevated temperature and inducing a reaction between salicylic acid and the dissolution-enhancing agent. According to the present invention, a high amount of salicylic acid can be stabilized in a solubilizing formulation without decreasing stability over time (precipitation).

In an aspect, an object of the present invention is to provide a salicylic acid aqueous solution in which the water-solubility of salicylic acid is enhanced.

In another aspect, an object of the present invention is to provide a salicylic acid aqueous solution in which salicylic acid is stabilized and is not precipitated as crystals without containing a separate solvent in an excessive amount.

In an aspect, the present invention may provide a salicylic acid aqueous solution which exhibits good stability over wide temperature range.

In an aspect, the present invention provides a salicylic acid aqueous solution comprising salicylic acid, tromethamine as a dissolution-enhancing agent to enhance dissolution of salicylic acid, and water for dissolving salicylic acid.

In an aspect, salicylic acid salt formed in high temperature has excellent hydrophilic property, so crystals are not generated when observed at different temperature conditions. Therefore, a salicylic acid aqueous solution for solubilizing a high amount of salicylic acid that is stable for a long term can be produced.

In an aspect, the present invention may provide various solubilizing and emulsion formulations.

In an aspect, according to the present invention, a high amount of salicylic acid can be stabilized in a cosmetic formulation without containing a separate solvent. Therefore, the present invention can be widely applicable to various cosmetic formulations (such as skin care, make up and personal care).

BRIEF DESCRIPTION OF THE DRAWINGS

FIG. 1 shows the result of observing the stability of emulsion formulations according to the present invention at different temperature conditions for 4 weeks and the result of observing the stability immediately after the preparation of formulations dissolved in ethanol according to a conventional method.

DETAILED DESCRIPTION OF THE PREFERRED EMBODIMENTS

Hereinafter, the embodiments according to the present invention will be described in more detail. However, the techniques disclosed in this application are not limited to the embodiments described herein but may be variously embodied. However, it should be understood that the embodiments disclosed herein are provided so that this disclosure will be thoroughly and completely described and will fully convey the scope of the invention to those skilled in the art. Moreover, those skilled in the art can variously realize the present invention without departing from the sprite of the present invention.

In an aspect, the present invention provides a salicylic acid aqueous solution comprising salicylic acid, tromethamine as a dissolution-enhancing agent to enhance dissolution of salicylic acid, and water for dissolving salicylic acid.

Salicylic acid used in the present invention is a representative insoluble material. Salicylic acid has a molecular structure to be favorably crystallized through n bonds between benzene molecules, so it can be easily precipitated as crystals in an aqueous solution.

In an embodiment, the salicylic acid aqueous solution may comprise 0.5 to 20 wt % of salicylic acid based on a total weight of the aqueous solution. In particular, if an amount of salicylic acid is less than 0.5 wt % based on a total weight of the aqueous solution, it may be difficult to obtain a significant effect of salicylic acid. If the amount is more than 20 wt % based on a total weight of the aqueous solution, there may be severe skin irritation when it is used as a topical skin agent. Preferably, the aqueous solution may comprise 1 to 5 wt % of salicylic acid based on a total weight of the aqueous solution.

Specifically, the salicylic acid aqueous solution may comprise at least 0.5 wt %, at least 0.6 wt %, at least 0.7 wt %, at least 0.8 wt %, at least 0.9 wt %, at least 1.0 wt %, at least 1.1 wt %, at least 1.2 wt %, at least 1.3 wt %, at least 1.4 wt %, at least 1.5 wt %, at least 1.6 wt %, at least 1.7 wt %, at least 1.8 wt %, at least 1.9 wt %, at least 2.0 wt %, at least 2.1 wt %, at least 2.2 wt %, at least 2.3 wt %, at least 2.4 wt %, at least 2.5 wt %, at least 2.6 wt %, at least 2.7 wt %, at least 2.8 wt %, at least 2.9 wt %, at least 3.0 wt %, at least 4.0 wt %, at least 5.0 wt %, at least 6.0 wt %, at least 7.0 wt %, at least 8.0 wt %, at least 9.0 wt %, at least 10 wt %, at least 11 wt %, at least 12 wt %, at least 13 wt %, at least 14 wt %, at least 15 wt %, at least 16 wt %, at least 17 wt %, at least 18 wt %, at least 19 wt % of salicylic acid based on a total weight of the aqueous solution, and may comprise up to 20.0 wt %, up to 19 wt %, up to 18 wt %, up to 17 wt %, up to 16 wt %, up to 15 wt %, up to 14 wt %, up to 13 wt %, up to 12 wt %, up to 11 wt %, up to 10 wt %, up to 9.0 wt %, up to 8.0 wt %, up to 7.0 wt %, up to 6.0 wt %, up to 5.0 wt %, up to 4.0 wt %, up to 3.0 wt %, up to 2.9 wt %, up to 2.8 wt %, up to 2.7 wt %, up to 2.6 wt %, up to 2.5 wt %, up to 2.4 wt %, up to 2.3 wt %, up to 2.2 wt %, up to 2.1 wt %, up to 2.0 wt %, up to 1.9 wt %, up to 1.8 wt %, up to 1.7 wt %, up to 1.6 wt %, up to 1.5 wt %, up to 1.4 wt %, up to 1.3 wt %, up to 1.2 wt %, up to 1.1 wt %, up to 1.0 wt %, up to 0.9 wt %, up to 0.8 wt %, up to 0.7 wt %, up to 0.6 wt % of salicylic acid based on a total weight of the aqueous solution.

In an embodiment, tromethamine is a component having EWG green grade which may be usefully used in the cosmetic area. Tromethamine may have a good effect in terms of skin stability in use.

In an embodiment, the salicylic acid aqueous solution may comprise a dissolution-enhancing agent of at least 85 parts by weight, for example in the range of 85 to 110 parts by weight, based on 100 parts by weight salicylic acid. If the dissolution-enhancing agent is less than 85 parts by weight based on 100 parts by weight salicylic acid, there may be crystal precipitation due to excess salicylic acid which is not involved in a reaction with the dissolution-enhancing agent.

Specifically, the salicylic acid aqueous solution may comprise the dissolution-enhancing agent of at least 85 parts by weight, at least 86 parts by weight, at least 87 parts by weight, at least 88 parts by weight, at least 89 parts by weight, at least 90 parts by weight, at least 91 parts by weight, at least 92 parts by weight, at least 93 parts by weight, at least 94 parts by weight, at least 95 parts by weight, at least 96 parts by weight, at least 97 parts by weight, at least 98 parts by weight, at least 99 parts by weight, at least 100 parts by weight, at least 101 parts by weight, at least 102 parts by weight, at least 103 parts by weight, at least 104 parts by weight, at least 105 parts by weight, at least 106 parts by weight, at least 107 parts by weight, at least 108 parts by weight, at least 109 parts by weight, or at least 110 parts by weight based on 100 parts by weight salicylic acid. Furthermore, the salicylic acid aqueous solution may comprise the dissolution-enhancing agent of up to 110 parts by weight, up to 109 parts by weight, up to 108 parts by weight, up to 107 parts by weight, up to 106 parts by weight, up to 105 parts by weight, up to 104 parts by weight, up to 103 parts by weight, up to 102 parts by weight, up to 101 parts by weight, up to 100 parts by weight, up to 99 parts by weight, up to 98 parts by weight, up to 97 parts by weight, up to 96 parts by weight, up to 95 parts by weight, up to 94 parts by weight, up to 93 parts by weight, up to 92 parts by weight, or up to 91 parts by weight based on 100 parts by weight salicylic acid.

When the salicylic acid aqueous solution comprises 85 to 110 parts by weight the dissolution-enhancing agent based on 100 parts by weight salicylic acid, it can remain stable without salicylic acid crystal precipitation.

In an aspect, the aqueous solution according to the present invention may further comprise a thickener.

As the thickener, one or more selected from the group consisting of methyl cellulose, carboxy methyl cellulose, carboxy methyl hydroxy guanine, hydroxy methyl cellulose, hydroxyethylcellulose, carboxy vinyl polymer, polyquaternium, cetearyl alcohol, stearic acid, carrageenan, carbomers, acrylate/C-30 alkyl acrylate crosspolymer, glyceryl acrylate/acrylic acid copolymer, xanthan gum, dehydroxanthan gum, magnesium aluminum silicate, methylcellulose, bentonite, *Ceratonia siliqua* gum, cellulose gum, sodium magnesium silicate, sodium polyacrylate, acrylate copolymer, ammonium acryloyldimethyltaurateVP copolymer, corn starch, Gellan Gum, polyacrylate-13, polyacrylate crosspolymer, polyacrylamide, PEG-240/HDI copolymerbis-decyltetradeceth-20ether, hydroxy ethyl acrylate/sodium acryloyldimethyltaurate copolymer, hydroxypropyl starch phosphate, and hydrolyzed wheat protein/PVP crosspolymer may be used. In an embodiment, the thickener may be carbomers.

In an embodiment, the aqueous solution may comprise 0.01 to 20.0 wt % of the thickener based on a total weight of the aqueous solution. Specifically, it may comprise the thickener of at least 0.5 wt %, at least 0.6 wt %, at least 0.7 wt %, at least 0.8 wt %, at least 0.9 wt %, at least 1.0 wt %, at least 1.1 wt %, at least 1.2 wt %, at least 1.3 wt %, at least 1.4 wt %, at least 1.5 wt %, at least 1.6 wt %, at least 1.7 wt %, at least 1.8 wt %, at least 1.9 wt %, at least 2.0 wt %, at least 2.1 wt %, at least 2.2 wt %, at least 2.3 wt %, at least 2.4 wt %, at least 2.5 wt %, at least 2.6 wt %, at least 2.7 wt %, at least 2.8 wt %, at least 2.9 wt %, at least 3.0 wt %, at least 4.0 wt %, at least 5.0 wt %, at least 6.0 wt %, at least 7.0 wt %, at least 8.0 wt %, at least 9.0 wt %, at least 10 wt %, at least 11 wt %, at least 12 wt %, at least 13 wt %, at least 14 wt %, at least 15 wt %, at least 16 wt %, at least 17 wt %, at least 18 wt %, at least 19 wt %, and up to 20.0 wt %, up to 19 wt %, up to 18 wt %, up to 17 wt %, up to 16 wt %, up to 15 wt %, up to 14 wt %, up to 13 wt %, up to 12 wt %, up to 11 wt %, up to 10 wt %, up to 9.0 wt %, up to 8.0 wt %, up to 7.0 wt %, up to 6.0 wt %, up to 5.0 wt %, up to 4.0 wt %, up to 3.0 wt %, up to 2.9 wt %, up to 2.8 wt %, up to 2.7 wt %, up to 2.6 wt %, up to 2.5 wt %, up to 2.4 wt %, up to 2.3 wt %, up to 2.2 wt %, up to 2.1 wt %, up to 2.0 wt %, up to 1.9 wt %, up to 1.8 wt %, up to 1.7 wt %, up to 1.6 wt %, up to 1.5 wt %, up to 1.4 wt %, up to 1.3 wt %, up to 1.2 wt %, up to 1.1 wt %, up to 1.0 wt %, up to 0.9 wt %, up to 0.8 wt %, up to 0.7 wt %, or up to 0.6 wt %. If the thickener is in the range indicated above, a proper viscosity can be secured.

In one aspect of the present invention, the salicylic acid aqueous solution may have a viscosity of 10 to 20000 cps.

Specifically, said viscosity may be at least 10 cps, at least 100 cps, at least 200 cps, at least 300 cps, at least 400 cps, at least 500 cps, at least 600 cps, at least 700 cps, at least 800 cps, at least 900 cps, at least 1000 cps, at least 2000 cps, at least 3000 cps, at least 4000 cps, at least 5000 cps, at least 6000 cps, at least 7000 cps, at least 8000 cps, at least 9000 cps, at least 10000 cps, at least 11000 cps, at least 12000 cps, at least 13000 cps, at least 14000 cps, at least 15000 cps, at least 16000 cps, at least 17000 cps, at least 18000 cps, at least 19000 cps, or at least 20000 cps, and up to 20000 cps, up to 19000 cps, up to 18000 cps, up to 17000 cps, up to 16000 cps, up to 15000 cps, up to 14000 cps, up to 13000 cps, up to 12000 cps, up to 11000 cps, up to 10000 cps, up to 9000 cps, up to 8000 cps, up to 7000 cps, up to 6000 cps, up to 5000 cps, up to 4000 cps, up to 3000 cps, up to 2000 cps, up to 1000 cps, up to 900 cps, up to 800 cps, up to 700 cps, up to 600 cps, up to 500 cps, up to 400 cps, up to 300 cps, up to 200 cps, up to 100 cps, or up to 10 cps.

Furthermore, the viscosity may be in the range of 2000 cps to 8000 cps or less. In the range of viscosity indicated above, the salicylic acid aqueous solution according to the present invention can also remain stable without salicylic acid crystal precipitation.

In an embodiment, the salicylic acid aqueous solution may have solubility of 1 to 20 mg/ml in water at room temperature. Specifically, it may be at least 1 mg/ml, at least 2 mg/ml, at least 3 mg/ml, at least 4 mg/ml, at least 5 mg/ml, at least 6 mg/ml, at least 7 mg/ml, at least 8 mg/ml, at least 9 mg/ml, at least 10 mg/ml, at least 11 mg/ml, at least 12 mg/ml, at least 13 mg/ml, at least 14 mg/ml, at least 15 mg/ml, at least 16 mg/ml, at least 17 mg/ml, at least 18 mg/ml, at least 19 mg/ml, or at least 20 mg/ml. If the aqueous solution has solubility within the range indicated above, good stability can be obtained when it is used, for example in W/O formulation or O/W formulation cosmetic compositions, as low viscosity water skin formulation or emulsion formulation.

In an aspect, the aqueous solution according to the present invention may further comprise caffeine.

Generally, caffeine has poor stability when it is present at high concentration in an aqueous solution. However, when the salicylic acid aqueous solution according to one embodiment of the present invention contains caffeine, it can have good thermal stability even when it contains caffeine at high concentration.

As such, in an aspect of the present invention, a cosmetic composition comprising an aqueous phase containing the salicylic acid aqueous solution and oily phase can also have good thermal stability even though it contains caffeine at high concentration.

In an embodiment, the aqueous solution according to the present invention may comprise caffeine of 100 to less than 400 parts by weight based on 100 parts by weight salicylic acid. For example, it may comprise caffeine of at least 150 parts by weight, at least 200 parts by weight, at least 250 parts by weight, at least 300 parts by weight, or at least 350 parts by weight based on 100 parts by weight salicylic acid, and for example, the caffeine of up to 350 parts by weight, up to 300 parts by weight, up to 250 parts by weight, up to 200 parts by weight, or up to 150 parts by weight based on 100 parts by weight salicylic acid.

If the caffeine is less than 100 parts by weight based on 100 parts by weight salicylic acid, an effect due to caffeine may be minor, and if the caffeine is more than 400 parts by weight based on 100 parts by weight salicylic acid, the aqueous solution may have low thermal stability.

In an embodiment, caffeine may be 1 to less than 4 wt % based on a total weight of the aqueous solution. For example, caffeine may be at least 1.25 wt %, at least 1.5 wt %, at least 1.75 wt %, at least 2.0 wt %, at least 2.25 wt %, at least 2.5 wt %, at least 2.75 wt %, at least 3.0 wt %, at least 3.25 wt %, at least 3.5 wt %, or at least 3.75 wt % based on a total weight of the aqueous solution, and for example, caffeine may be up to 3.75 wt %, up to 3.5 wt %, up to 3.25 wt %, up to 3.0 wt %, up to 2.75 wt %, up to 2.5 wt %, up to 2.25 wt %, up to 2.0 wt %, up to 1.75 wt %, up to 1.5 wt %, up to 1.25 wt % based on a total weight of the aqueous solution.

If the caffeine is less than 1 wt % based on a total weight of the aqueous solution, an effect due to caffeine may be minor, and if the caffeine is 4 wt % or more based on 100 parts by weight salicylic acid, the aqueous solution may have low thermal stability.

In an aspect, the present invention may provide a cosmetic composition comprising an aqueous phase containing a salicylic acid aqueous solution and an oily phase.

According to an embodiment, the above-mentioned oily phase may employ, for example, non-polar hydrocarbon-based oils such as hexane, octane, decane, dodecane, tetradecane, hexadecane, mineral oil, liquid paraffine, isohexadecane, isododecane, ozokerite, hydrogenated poly(C6-14) olefin, hydrogenated polydecene, squalane, squalene, paraffine, isoparaffine, ceresin, vaseline, dimethicone, decamethylcyclopentasiloxane, hydrogenated polyisobutene, but not limited to these materials.

Water such as distilled water and deionized water may be used.

The oily phase may comprise 5.0 wt % to 30.0 wt % based on a total weight of the composition. For example, the oily phase may comprise at least 5.0 wt %, at least 6.0 wt %, at least 7.0 wt %, at least 8.0 wt %, at least 9.0 wt %, at least 10.0 wt %, at least 11.0 wt %, at least 12.0 wt %, at least 13.0 wt %, at least 14.0 wt %, at least 15.0 wt %, at least 16.0 wt %, at least 17.0 wt %, at least 18.0 wt %, at least 19.0 wt %, at least 20.0 wt %, at least 21.0 wt %, at least 22.0 wt %, at least 23.0 wt %, at least 24.0 wt %, at least 25.0 wt %, at least 26.0 wt %, at least 27.0 wt %, at least 28.0 wt %, at least 29.0 wt %, or at least 30.0 wt %, and up to 30.0 wt %, up to 29.0 wt %, up to 28.0 wt %, up to 27.0 wt %, up to 26.0 wt %, up to 25.0 wt %, up to 24.0 wt %, up to 23.0 wt %, up to 22.0 wt %, up to 21.0 wt %, up to 20.0 wt %, up to 19.0 wt %, up to 18.0 wt %, up to 17.0 wt %, up to 16.0 wt %, up to 15.0 wt %, up to 14.0 wt %, up to 13.0 wt %, up to 12.0 wt %, up to 11.0 wt %, up to 10.0 wt %, up to 9.0 wt %, up to 8.0 wt %, up to 7.0 wt %, or up to 6.0 wt %, based on a total weight of the composition. If the oily phase is in the range indicated above, the cosmetic composition can form a stable emulsion formulation and maintain stability over time.

In another aspect, the cosmetic composition may be a W/O or O/W formulation.

According to embodiments of the present invention, the cosmetic composition may be formulated with a cosmetically or dermatologically acceptable medium or base material. The cosmetic composition may be provided as any formulation suitable for topical application, for example in the form of suspension, microemulsion, microcapsule, microgranule or ionic(liposome) and non-ionic vesicle dispersion, or in the form of cream, skin, lotion, powder, ointment, spray, or conceal stick. Furthermore, it may be used in a foam or aerosol composition with propellant. These compositions may be prepared according to common methods known in the art.

According to embodiments of the present invention, the cosmetic composition may contain an adjuvant commonly used in the cosmetic or dermatological area such as fat substances, organic solvents, dissolving agents, concentrating agents, gelling agents, anti-oxidants, suspending agents, stabilizing agents, foaming agents, flavoring agents, water, ionic or non-ionic emulsifier, non-ionic emollient, filler, metallic ion blocker, chelating agents, preservatives, vitamins, blocking agents, wetting agents, essential oils, dyes, pigments, hydrophilic or lipophilic active agents, lipid vesicles, or other components commonly used in the cosmetics. These adjuvants are introduced in an amount generally used in the cosmetic or dermatological area.

According to embodiments of the present invention, the cosmetic composition may further contain a skin absorption-promoting material to enhance an effect of skin improvement.

In an aspect, the present invention may provide a method of preparing a salicylic acid aqueous solution comprising mixing salicylic acid with a dissolution-enhancing agent at a temperature of at least about 85° C.

In an embodiment, the above-mentioned temperature may be at least 85° C., at least 86° C., at least 87° C., at least 88° C., at least 89° C., at least 90° C., at least 91° C., at least 92° C., at least 93° C., at least 94° C., or at least 95° C., for example, 85 to 95° C., 86 to 94° C., 87 to 93° C., 88 to 92° C., 89 to 91° C. If a salicylic acid aqueous solution is prepared in the temperature range indicated above, the solubility of salicylic acid can be maximized in the resulting salicylic acid aqueous solution.

In an embodiment, the method may further comprise adding a thickener.

By adding a thickener, the viscosity of the resulting salicylic acid aqueous solution may be adjusted.

Now, the present invention will be described in more detail with reference to examples, comparative examples and experimental examples. It will be obvious to a person skilled in the art that these examples are only provided to more specifically describe the present invention but not intended to limit the present invention to these examples.

[Preparation Example 1] Preparation of Salicylic Acid Aqueous Solution

Salicylic acid and tromethamine as a stabilizing agent were put into proper amount of water as shown in Table 1. The mixture was stirred for 20 minutes or more at 90° C. to ensure a sufficient reaction of salicylic acid and tromethamine. Then, the mixture was cooled to room temperature to produce a salicylic acid aqueous solution.

TABLE 1

| Component (wt %) | Example 1 | Example 2 | Example 3 | Comparative example 1 | Comparative example 2 |
|---|---|---|---|---|---|
| Distilled water | To 100 | To 100 | To 100 | To 100 | To 100 |
| Salicylic acid | 2.0 | 2.0 | 2.0 | 0.6 | 0.6 |
| Tromethamine | 1.8 | 0.6 | 1.2 | 0 | 0 |
| Ethanol | 0 | 0 | 0 | 4.0 | 8.0 |

Examples 1 to 3 were prepared as described in the preparation example 1 with varying the amount of tromethamine in 2.0 wt % salicylic acid, and comparative examples 1 and 2 were prepared by a conventional method using ethanol with varying the amount of ethanol in 0.6 wt % salicylic acid.

[Experimental Example 1] Confirmation of Thermal Stability of Salicylic Acid Aqueous Solution Salicylic acid crystal precipitation was confirmed using aqueous solutions prepared in the preparation example 1 at various temperature conditions. The compositions prepared in the preparation example 1 were observed at −20° C. (freezing-thawing), 4° C. (cooling), 25° C. (room temperature), and 45° C., and in a 12 hour-cycle with varying temperatures from −20° C. to 45° C. to confirm the stability by observing salicylic acid crystal precipitation.

In particular, example 1 and comparative example 2 were observed for 4 weeks, and examples 2 and 3 and comparative example 1 were observed the next day. The stability of freezing-thawing sample was confirmed at room temperature. The result is shown in Table 2.

TABLE 2

| Temperature | Example 1 | Example 2 | Example 3 | Comparative example 1 | Comparative example 2 |
|---|---|---|---|---|---|
| 45° C. | X | ○ | X | X | X |
| Room temperature | X | ○ | ○ | X | X |
| Cooling | X | ○ | ○ | ○ | X |
| Freezing-thawing | X | ○ | ○ | ○ | X |
| Cycle | X | ○ | ○ | ○ | X |

○: unstable (precipitated),
X: stable (not precipitated)

When aqueous solutions of salicylic acid were prepared using different amounts of a stabilizing agent (tromethamine), if the amount of stabilizing agent in the solution is 90% or more with respect to the amount of salicylic acid, salicylic acid crystals were not precipitated over the whole temperature range indicated above. That is, it was confirmed that this solution has thermal stability (the freezing-thawing sample was confirmed at room temperature).

If the amount of stabilizing agent is not sufficient as in examples 2 and 3, salicylic acid was not fully reacted with the stabilizing agent and excess salicylic acid was precipitated as crystals with decreasing temperature.

In comparative examples 1 and 2, aqueous solutions were prepared using ethanol by the conventional method instead of the method described in the preparation example 1, and salicylic acid crystal precipitation was observed at various temperature range.

As seen in comparative examples 1 and 2, it was confirmed that at least ethanol of at 10 times is required to fully dissolve 0.6 wt % salicylic acid, which was an amount relatively smaller than examples 1 to 3. Therefore, it was confirmed that salicylic acid crystals precipitated in 4 wt % ethanol, which is generally used for solubilizing the cosmetics.

It is expected that about 0.6 wt % salicylic acid can be dissolved in up to 15 wt % ethanol, which is an amount used for the common cosmetic formulation. Therefore, comparative examples 1 and 2 employ 0.6 wt % salicylic acid to prepare formulations.

The salicylic acid aqueous solutions as prepared in the preparation example 1 were observed for crystallization at different temperature conditions. It was confirmed that the aqueous solution of example 1 according to the present invention remained stable without crystallization of salicylic acid. When a solubilized aqueous solution and an emulsion formulation was prepared using 8 wt % ethanol and said aqueous solution as aqueous phase, salicylic acid was not precipitated in the formulation as well.

[Experimental Example 2] Confirmation of Stability of Emulsion Formulations Prepared Using Salicylic Acid Aqueous Solutions As shown in Table 3, emulsion formulations were prepared with the salicylic acid aqueous solutions prepared using the salicylic acid-stabilizing agent reaction according to the present invention. The resulting formulations were observed for stability.

TABLE 3

|  | Raw material | Example 4 | Comparative example 3 |
|---|---|---|---|
| Water phase | Distilled water | To 100 | To 100 |
|  | Salicylic acid | 2.0 | 0 |
|  | Tromethamine | 1.9 | 0 |
|  | Disodium EDTA | 0.02 | 0.02 |
|  | Propanediol | 8.0 | 8.0 |
|  | Betain | 1.0 | 1.0 |
| Ethanol phase | Ethanol | 0 | 5.0 |
|  | PEG 60 hydrogenated castor oil | 0.3 | 0.3 |
|  | Octyldodeceth-16 | 0.2 | 0.2 |
|  | Hexanediol | 0.7 | 0.7 |
|  | Ethylhexylglycerine | 0.05 | 0.05 |
|  | Salicylic acid | 0 | 2.0 |
|  | Fragrance | 0.1 | 0.1 |

As seen in Table 3, example 4 was compared with comparative example 3 and the result is shown in FIG. 1. Example 4 is a cosmetic composition prepared using the solubilized aqueous solution according to the present invention, and comparative example 3 is prepared by the conventional method using ethanol wherein salicylic acid is dissolved in ethanol and added to the common solubilizing regimen.

When example 4 was observed for stability for 4 weeks in a clear solution state, it was confirmed that salicylic acid did not precipitate. To the contrary, in comparative example 3, salicylic acid was precipitated at all temperatures within a week after preparation. Especially, comparative example 3 showed that salicylic acid crystals were precipitated immediately after preparation and prior to confirmation of 4 week-stability, and therefore confirmed that this formulation has low stability.

From experimental example 2, it was confirmed that the solubilized aqueous solution according to the present invention has good salicylic acid stability.

[Preparation Example 2] Preparation of Aqueous Solutions Having a High Amount of Caffeine The salicylic acid aqueous solutions were prepared using the same method as in the preparation example 1, except for adding caffeine according to the amounts as shown in Table 4.

TABLE 4

|  | Exam. 5 | Exam. 6 | Exam. 7 | Exam. 8 | Exam. 9 | Com. Exam. 4 | Com. Exam. 5 |
|---|---|---|---|---|---|---|---|
| Distilled water | To 100 | To 100 | To 100 | To 100 | To 100 | To 100 | To 100 |
| Salicylic acid | 1 | 1 | 1 | 1 | 1 | 1 | 1 |
| Tromethamine | 0.9 | 0.9 | 0.9 | 0.9 | 0.9 | 0.9 | 0.9 |
| Caffeine | 1.5 | 3 | 3.25 | 3.5 | 3.75 | 4 | 4.5 |

[Experimental Example 3] Confirmation of Thermal Stability of Aqueous Solutions Having a High Amount of Caffeine The aqueous solutions of salicylic acid/caffeine prepared in preparation example 2 were observed for caffeine precipitation for 4 weeks under room temperature/cooling/freezing-thawing conditions. For the cooling/freezing-thawing sample, caffeine crystal precipitation was observed after removing the sample from a thermostatic bath and leaving it at room temperature for 6 hours. The result is shown in Table 5.

TABLE 5

|  | Room temp. | Cooling (4° C.) | Freezing-thawing |
|---|---|---|---|
| Example 5 | X | X | X |
| Example 6 | X | X | X |
| Example 7 | X | X | X |
| Example 8 | X | X | X |
| Example 9 | X | X | X |
| Comparative example 4 | X | X | ○ |
| Comparative example 5 | X | ○ | ○ |

From the result of experimental example 3, it was confirmed that the aqueous solution according to the present invention has good thermal stability even though it contains a high amount of caffeine. However, comparative examples 4 and 5, which contain 4 wt % or more of caffeine, caffeine crystals were precipitated at the freezing-thawing condition (comparative example 4) and both the freezing-thawing and cooling conditions (comparative example 5).

[Experimental Example 4] Confirmation of Stability of Emulsion Formulation Prepared Using the Aqueous Solution with a High Amount of Caffeine As shown in Table 6, formulations were prepared with caffeine amounts used in examples 8 and 9, and comparative example 4. Caffeine precipitation was compared between simple salicylic acid/caffeine aqueous solutions and the resulting formulations (the amount is in wt %).

TABLE 6

| Raw material | Example 10 | Example 11 | Example 12 |
|---|---|---|---|
| Distilled water | To 100 | To 100 | To 100 |
| Disodium EDTA | 0.05 | 0.05 | 0.05 |
| Butyleneglycol | 8 | 8 | 8 |
| Glycerine | 4 | 4 | 4 |
| Salicylic acid | 1.0 | 1.0 | 1.0 |
| Tromethamine | 0.9 | 0.9 | 0.9 |
| Caffeine | 3.5 | 3.75 | 4 . 0 |
| Ethanol | 4 | 4 | 4 |
| PGG60 hydrogenated castor oil | 0.4 | 0.4 | 0.4 |
| Glyceryl caprylate | 0.1 | 0.1 | 0.1 |

TABLE 6-continued

| Raw material | Example 10 | Example 11 | Example 12 |
|---|---|---|---|
| Ethylhexyl glycerine | 0.05 | 0.05 | 0.05 |
| Fragrance | 0.05 | 0.05 | 0.05 |

Caffeine precipitation was observed under room temperature/cooling/freezing-thawing conditions for 4 weeks using the same method as in experimental example 3. The result is shown in Table 7.

TABLE 7

|  | Room temp. | Cooling (4° C.) | Freezing-thawing |
|---|---|---|---|
| Example 10 | X | X | X |
| Example 11 | X | X | X |
| Example 12 | X | X | X |

From the result of the experimental example 4, it was confirmed that examples 10 to 12 have good thermal stability because caffeine crystals were not precipitated in all examples 10 to 12 when they were applied to an emulsion formulation. Especially, in the aqueous solution of salicylic acid/caffeine as described in experimental example 3, when the sample with 4% caffeine is returned to room temperature, caffeine was still precipitated. To the contrary, in example 12, the resulting formulation with 4% caffeine had thermal stability because probably the formulation additionally contains polyol and ethanol which serve to dissolve caffeine in the formulation.

The examples described above should not be construed as limiting the technical idea of the present invention. The present invention is limited only by those described in claims, and those skilled in the art will be able to variously modify the technical idea of the present invention. Accordingly, such modifications will fall within the scope of the present invention as long as they are obvious to those skilled in the art.

What is claimed is:

1. A process of producing a salicylic acid and caffeine aqueous solution, the process comprising:
   (a) adding a salicylic acid in an amount of no less than 0.5 to no more than 20 wt % based on the total weight of the salicylic acid and caffeine aqueous solution, caffeine in an amount of about 1 to about 3.75 wt % based on the total weight of the salicylic acid and caffeine aqueous solution, and tromethamine in an amount of at least 90 parts by weight based on 100 parts by weight of the salicylic acid, to water to obtain a mixture, and stirring the mixture,
   wherein the tromethamine acts as a dissolution-enhancing agent to enhance the dissolution of salicylic acid and caffeine,
   wherein the salicylic acid, caffeine, and tromethamine are added to the water in a single step, wherein the stirring of the mixture is carried out at a temperature of at least about 85° C.; and
   (b) forming a thermally stable salicylic acid and caffeine aqueous solution.

2. The process of claim 1, wherein the thermally stable salicylic acid and caffeine aqueous solution of step (b) is thermally stable for temperatures between −20° C. and 45° C.

3. The process of claim 2, wherein the salicylic acid and caffeine aqueous solution is prepared over a single 12-hour cycle, with varying temperatures of about −20° C. and to about 45° C. to confirm the thermal stability.

4. The process of claim 1, wherein the solubility of the salicylic acid and caffeine aqueous solution is 1 to 20 mg/ml in water at room temperature.

5. The process of claim 1, wherein the tromethamine added in an amount of at least 90 parts by weight based on 100 parts by weight of the salicylic acid, does not create a crystal precipitation of salicylic acid.

6. The process of claim 1, wherein (a) further comprises adding a thickener to the water.

7. The process of claim 6, wherein the thickener is one or more selected from the group consisting of methyl cellulose, carboxy methyl cellulose, carboxy methyl hydroxy guanine, hydroxy methyl cellulose, hydroxyethylcellulose, carboxy vinyl polymer, polyquaternium, cetearyl alcohol, stearic acid, carrageenan, carbomers, acrylate/C-30 alkyl acrylate crosspolymer, glyceryl acrylate/acrylic acid copolymer, xanthan gum, dehydroxanthan gum, magnesium aluminum silicate, bentonite, *Ceratonia siliqua* gum, cellulose gum, sodium magnesium silicate, sodium polyacrylate, acrylate copolymer, ammonium acryloyldimethyltaurate/VP copolymer, corn starch, gellan gum, polyacrylate-13, polyacrylate crosspolymer, polyacrylamide, PEG-240/HDI copolymer bis-decyltetradeceth-20 ether, hydroxy ethyl acrylate/sodium acryloyldimethyltaurate copolymer, hydroxypropyl starch phosphate, and hydrolyzed wheat protein/PVP crosspolymer.

8. The process of claim 6, comprising the thickener in an amount of 0.01 to 20.0 wt % based on the total weight of the salicylic acid and caffeine aqueous solution.

9. The process of claim 1, comprising caffeine in an amount of 100 to less than 400 parts by weight based on 100 parts by weight salicylic acid, and wherein the salicylic acid and caffeine aqueous solution is thermally stable despite the high concentration of the caffeine.

10. The process of claim 1, wherein the salicylic acid and caffeine aqueous solution has the viscosity of 10 to 20,000 cps.

\* \* \* \* \*